United States Patent
Taguchi

(10) Patent No.: US 7,209,541 B2
(45) Date of Patent: Apr. 24, 2007

(54) X-RAY ANALYSIS APPARATUS

(75) Inventor: Takeyoshi Taguchi, Tachikawa (JP)

(73) Assignee: Rigaku Corporation, Akishima-Shi, Tokyo (JP)

( * ) Notice: Subject to any disclaimer, the term of this patent is extended or adjusted under 35 U.S.C. 154(b) by 75 days.

(21) Appl. No.: 10/963,829

(22) Filed: Oct. 14, 2004

(65) Prior Publication Data

US 2005/0084065 A1 Apr. 21, 2005

(30) Foreign Application Priority Data

Oct. 17, 2003 (JP) ............................. 2003-357582

(51) Int. Cl.
*G01N 23/20* (2006.01)
(52) U.S. Cl. .................................................. 378/71
(58) Field of Classification Search ................ 378/71
See application file for complete search history.

(56) References Cited

U.S. PATENT DOCUMENTS

| 4,937,453 | A | * | 6/1990 | Nelson .................. 250/370.09 |
| 5,259,013 | A | * | 11/1993 | Kuriyama et al. ............ 378/43 |
| 5,526,394 | A | * | 6/1996 | Siczek et al. ................. 378/37 |
| 5,787,146 | A | * | 7/1998 | Giebeler ....................... 378/82 |
| 5,848,122 | A | * | 12/1998 | Kurtz ........................... 378/80 |
| 5,917,881 | A | * | 6/1999 | Jeffery ....................... 378/98.8 |
| 5,998,802 | A | | 12/1999 | Struye et al. |
| 6,710,341 | B2 | * | 3/2004 | Terauchi ...................... 250/310 |
| 2005/0058247 | A1 | * | 3/2005 | Taguchi et al. ............... 378/71 |

FOREIGN PATENT DOCUMENTS

JP 2002-116158 4/2002

OTHER PUBLICATIONS

T. Takeyoshi et al., "X-Ray Analysis Apparatus", filed Aug. 5, 2004, U.S. Appl. No. 10/911,564.
G. R. Davis et al., "X-ray microtomography scanner using time-delay integration for elimination of ring artefacts in the reconstructed image", Nuclear Instruments and Methods in Physics Research, Section A 394 (1997), pp. 157-162.
D. W. Holdsworth et al., "A time-delay integration charge-coupled device camera for slot-scanned digital radiography", Medical Physics, American Institute of Physics, vol. 1, Sep. 1, 1990, pp. 876-886.

* cited by examiner

*Primary Examiner*—Edward J. Glick
*Assistant Examiner*—Thomas R. Artman
(74) *Attorney, Agent, or Firm*—Buchanan Ingersoll & Rooney PC

(57) ABSTRACT

An X-ray analysis apparatus in which X-rays emitted from an X-ray source are applied to a sample and a two-dimensional CCD sensor detects the X-rays diffracted by the sample. The X-ray analysis apparatus includes a scan-moving means for scan-moving the two-dimensional CCD sensor in a plane, and a charge-transfer signal generating means for generating a charge-transfer signal in the CCD sensor, every time the CCD sensor is moved for a distance corresponding to the width of a pixel constituting the CCD sensor. Hence, the motion of the semiconductor X-ray detecting means and the generation of the charge-transfer signal are synchronized with each other to achieve time delay integration operation. Since the timing of transfer of electric charges in the CCD sensor is synchronized with scan-motion velocity of the CCD sensor, each pixel can accurately analyze the intensity of the X-ray diffracted at each diffraction angle.

11 Claims, 12 Drawing Sheets

(FT-TYPE)

(IT − TYPE)

X-RAY ANALYSIS APPARATUS

BACKGROUND OF THE INVENTION

1. Field of the Invention

The present invention relates to an X-ray analysis apparatus in which X-rays emitted from an X-ray source are applied to a sample and a semiconductor X-ray detecting means such as a CCD (Charge Coupled Device) sensor detects the X-rays diffracted by the sample.

2. Description of the Related Art

Most X-ray analysis apparatuses have an X-ray generating unit and an X-ray detector. The X-ray generating unit applies an X-ray to a sample. The X-ray detector detects the X-ray that is emerging from the sample. In the X-ray analysis apparatus, when an X-ray is applied to a sample and the incident angle of the X-ray with respect to the sample is set to be a specific angle, the X-ray is diffracted by the sample. The diffracted X-ray emerges from the sample. The X-ray, thus diffracted, is detected by the X-ray detector.

Various types of X-ray detectors are known, such as zero-dimensional X-ray detector, one-dimensional X-ray detector, and two-dimensional X-ray detector. These X-ray detectors are also known as zero-dimensional counter, one-dimensional counter and two-dimensional counter, respectively.

The zero-dimensional X-ray detector is an X-ray detector that is configured to detect X-rays as points. Examples of zero-dimensional X-ray detectors, known in the art, are PC (Proportional Counter) and SC (Scintillation Counter). The one-dimensional X-ray detector is an X-ray detector that is configured to detect X-rays as lines. Examples of one-dimensional X-ray detectors, known in the art, are PSPC (Position Sensitive Proportional Counter) and one-dimensional CCD sensor. The PSPC has linear signal lines, each generating an electric signal at the position where an X-ray is applied. The one-dimensional CCD sensor has a plurality of CCD elements arranged in a row.

The two-dimensional X-ray detector is an X-ray detector that is configured to detect X-rays in a plane. Examples of two-dimensional X-ray detectors, known in the art, are those known as imaging plate and two-dimensional CCD sensor. The imaging plate is a detector plate that has an X-ray receiving surface coated with storage phosphor. The two-dimensional CCD sensor has a plurality of CCD (Charge Coupled Device) elements arranged in rows and columns.

The CCD sensor described above used as the one-dimensional CCD sensor or two-dimensional CCD sensor is one of semiconductor position sensors. In recent years, various X-ray analysis apparatuses have been proposed, each comprising a semiconductor position sensor such as a CCD sensor as an X-ray detector. It is expected that X-ray analysis apparatuses of this type analyze X-rays faster than the zero-dimensional counter and the one-dimensional counter.

Conventionally, there is disclosed an X-ray analysis apparatus that uses a two-dimensional CCD sensor and optical fibers to obtain a two-dimensional diffraction image whose area is broader than the two-dimensional CCD sensor in e.g. Japanese Patent Laid-Open Publication No. 2002-116158, pp. 3–6, FIG. 1. The two-dimensional diffraction image is a diffraction image that is displayed two-dimensionally or in a plane, as shown in FIG. 8. In the conventional X-ray analysis apparatus disclosed in the publication, as shown in FIG. 6, a phosphor material 102 is arranged behind a sample 'S' when viewed from an X-ray source 101, and the phosphor material 102 has its light-outgoing surface (that is right side surface in FIG. 6) coupled to a bundle of plural optical fibers 103 with its longitudinal cross-section formed into a taper, and the optical fibers 103 has its light-outgoing end (that is right side end in FIG. 6) coupled to a two-dimensional CCD sensor 104.

In the conventional X-ray analysis apparatus, a diffracted X-ray emerging from the sample 'S' is applied to the phosphor material 102 to form a light image corresponding to the diffracted X-ray in the phosphor material 102. Then the light image is directed to the two-dimensional CCD sensor 104 by the optical fibers 103, and is accumulated in plural pixels of the CCD sensor 104 as electric charges. It is expected that X-ray analysis apparatuses of this type analyze X-rays faster than the zero-dimensional counter and the one-dimensional counter.

Each of the plural optical fibers 103 used in the conventional X-ray analysis apparatus has its longitudinal cross-section tapered so that the diameter of the optical fibers 103 at the phosphor material 102 side becomes large and that at the CCD sensor 104 side becomes small. This type of CCD sensor using thus tapered optical fibers 103 is referred to as a tapered CCD sensor. Generally, the CCD sensor 104 is cooled when in use.

When employing the conventional X-ray analysis apparatus using the tapered CCD sensor shown in FIG. 6, since the light image is distorted due to distortion of the optical fibers 103 themselves, there is raised a problem that data obtained by the CCD sensor is not correct. Furthermore, since the X-ray image is once converted to light by the phosphor material 102 and thus converted data is detected by the CCD sensor, there is also raised a problem that data obtained by the CCD sensor is not correct.

On the other hand, in case of using a two-dimensional CCD sensor to obtain a two-dimensional diffraction image whose area is broader than the receiving surface of the two-dimensional CCD sensor, other than the method shown in FIG. 6, there is proposed a method in which X-rays are detected while the sample being a subject and the two-dimensional CCD sensor being an X-ray detector are moving relative to each other. However, employing this method, the X-ray analysis apparatus can hardly detect X-rays at high speed and high sensitivity. This is because the spatial resolution of the conventional CCD sensor is approximately 100 μm at most, and the plural CCD pixels cannot obtain data or an image at high resolution when the sample and the two-dimensional CCD sensor move relative to each other at an excessively high speed.

SUMMARY OF THE INVENTION

The present invention has been made in view of the foregoing. An object of this invention is to provide an X-ray analysis apparatus which can form a two-dimensional diffraction image fast with high accuracy.

An X-ray analysis apparatus according to the present invention is of the type in which X-rays emitted from an X-ray source are applied to a sample and a semiconductor X-ray detecting means detects the X-rays diffracted by the sample. The apparatus includes: a scan-moving means for scan-moving the semiconductor X-ray detecting means in a plane; and a charge-transfer signal generating means for generating a charge-transfer signal in the semiconductor X-ray detecting means, every time the semiconductor X-ray detecting means is moved for a distance corresponding to the width of a pixel constituting the semiconductor X-ray detecting means. The motion of the semiconductor X-ray detecting means and the generation of the charge-transfer signal are synchronized with each other to achieve time delay integration operation.

The expression of "in a plane" means "not in a frequently irregular plane", and the plane includes an even plane and an uneven plane. The uneven plane includes a cylindrically curved plane and a plane which is curved into other forms.

The charge-transfer signal is a signal that, in sequentially transferring charges accumulated in respective plural pixels of the semiconductor X-ray detecting means among those plural pixels, indicates the transfer of charges. The signal is generally a pulse signal whose frequency is approximately 1 MHz.

In the X-ray analysis apparatus, the semiconductor X-ray detecting means is driven by the scan-moving means to be moved two-dimensionally or in a plane. The semiconductor X-ray detecting means can therefore detect X-rays that travel, after diffracted by the sample, along various diffraction angles in an area broader than the semiconductor X-ray detecting means. Since a broad area can be analyzed using a small semiconductor X-ray detecting means, the cost can be lowered as compared with the case using a large semiconductor X-ray detecting means.

Furthermore, since the timing of transfer of charges in the semiconductor X-ray detecting means is synchronized with scan-motion velocity of the semiconductor X-ray detecting means, the pixels of the semiconductor X-ray detecting means accumulate X-rays diffracted at the same angle. Hence, even when the semiconductor X-ray detecting means moves at high scan-motion velocity, each pixel can accurately analyze the intensity of the X-ray diffracted at each diffraction angle. This can accomplish an X-ray analysis of the sample, at a very high speed with high accuracy.

It is desired that the semiconductor X-ray detecting means used in the present invention be a CCD sensor. Specifically, an X-ray direct detection type CCD sensor which directly receives an X-ray to convert thus received X-ray to an electric signal is desired, in which a phosphor plate is not interposed.

Generally, the CCD sensor has a CCD (Charge Coupled Device) that transfers signal charges from potential wells to other potential wells. The region corresponding to one potential well is one pixel. The potential wells are arranged on an X-ray receiving surface in a one-dimensional pattern (that is, in a line), or in a two-dimensional pattern (that is, in a plane). To detect X-rays at high speed and high sensitivity, it is desirable to arrange the pixels in a two-dimensional pattern.

The potential wells are provided in, for example, such a MOS (Metal Oxide Semiconductor) structure that comprises metal electrodes 1, an oxide insulating layer 2, and a semiconductor layer 3, as shown in FIG. 5. More specifically, a potential well is formed when a voltage is applied to one of the electrodes 1, while a different voltage is applied to the other electrodes 1, thus setting that part of the layer 3 which lies beneath this electrode 1 at a particular potential, and setting the other parts of the layer 3 at a different potential. The signal charge confined in the potential well is sequentially transferred through the semiconductor layer 3 to an output unit. The charge-transfer signal is a signal that is sent to the CCD sensor when transferring the signal charge through the semiconductor layer 3.

A method of detecting X-rays by using a CCD sensor has been known. In this method, a phosphor plate is interposed between the CCD sensor and the sample. The X-rays emerging from the sample are applied to the phosphor plate, which emits light from the parts irradiated with the X-rays. The CCD sensor receives the light. By contrast, the semiconductor X-ray detecting means used in the present invention can directly detect X-rays, not through a phosphor plate. Further, the semiconductor X-ray detecting means generates electrons the number of which is proportional to the photon energy it has received.

The CCD sensor used as semiconductor X-ray detecting means in this invention may be a one-dimensional one or a two-dimensional one. Nonetheless, a two-dimensional CCD sensor is preferable. Various types of two-dimensional CCD sensors are available, such as FT (Frame Transfer) type, FFT (Full Frame Transfer) type, IT (Interline Transfer) type, and the like.

These types of two-dimensional CCD sensors will be described, using the terms "horizontal retrace period" and "vertical retrace period". These terms are generally used in explaining the process of reading and writing one-frame video data by scanning the reading point. As shown in FIG. 9, the horizontal retrace period is a time during which the reading point moves from one horizontal scanning line $S_H$ to the next horizontal scanning line $S_H$. The vertical retrace period is a time between one vertical scanning to the next. In other words, during this period, the reading point moves from the ending point $P_e$ of one frame to the starting point $P_S$ of the next frame.

As FIG. 2 shows, a two-dimensional CCD sensor of FT type has a light-receiving unit 6, a charge-accumulating unit 7, a horizontal shift register 8, and an output unit 9. The light-receiving unit 6 is a vertical shift register. The charge-accumulating unit 7 is a vertical shift register, too. Vertical shift registers are known also as "parallel registers". Horizontal shift registers are known also as "serial registers" or "reading registers". The light-receiving unit 6 has metal electrodes of the same type as the electrodes 1 (FIG. 5). The metal electrodes are made of transparent conductive material such as polysilicon.

When light is applied to the semiconductor layer 3 through the metal electrodes 1, photoelectric conversion is performed, generating signal charges. The signal charges are accumulated in the potential well lying beneath the electrodes 1. The signal charges are transferred in units of frames, at high speed to the charge-accumulating unit 7 during the vertical retrace period, i.e., the period between one vertical scanning and the next vertical scanning. Thus, in the FT-type CCD sensor, the light-receiving unit 6, which is a vertical shift register, functions as a photoelectric converter during the signal-accumulating period. While the photoelectric conversion is going on by the light-receiving unit 6, thus accumulating signals, the signal charges are transferred from the charge-accumulating unit 7 to the horizontal shift register 8, in units of lines, during the horizontal retrace period, i.e., the period between one horizontal scanning and the next horizontal scanning. They are further transferred from the horizontal shift register 8 to the output unit 9.

As FIG. 3 shows, a two-dimensional CCD sensor of FFT type has basically the same configuration as the FT-type CCD sensor of FIG. 2, but does not have charge-accumulating unit 7. Without a charge-accumulating unit 7, the FFT-type CCD sensor has a shutter mechanism at the light-receiving unit 6. In the FFT-type CCD sensor, charges are accumulated in the potential wells (i.e., pixels) of the light-receiving unit 6 during the signal-accumulating period. While the shutter mechanism remains closed, the signal charges are transferred to the output unit 9 via the horizontal shift register 8. Having no charge-accumulating units, the FFT-type CCD sensor can have more pixels than the FT-type CCD sensor if it has the same size as the FT-type CCD sensor. Alternatively, its light-receiving unit 6 may have a larger area.

As FIG. 4 depicts, a CCD sensor of IT type has a light-receiving unit 6, vertical shift registers 7, transfer gates 11, a horizontal shift register 8, and the output unit 9. The light-receiving unit 6 has photodiodes 6a arranged in rows. The vertical shift registers 7 are arranged to sandwich the photodiode 6a. Each transfer gate 11, which operate as a switch, is provided between a row of the photodiodes 6a and a shift register 7.

Each photodiode 6a performs photoelectric conversion, generating a signal charge. The signal charge generated by the photodiode 6a is accumulated in a coupling capacitor provided in the photodiode 6a. The signal charge is transferred from the photodiode 6a to the vertical shift register 7 via the transfer gate 11 during the vertical retrace period. The signal charges are transferred from the photodiodes 6a to the vertical shift registers 7 at the same time, unlike in the FT-type CCD sensor (see FIG. 2). Thereafter, the signal charges are transferred to the horizontal shift register 8, in units of lines during the horizontal retrace period. They are ultimately output from the horizontal shift register 8 to the output unit 9.

It is desired that the X-ray analysis apparatus of the present invention further comprises a display means for displaying a two-dimensional diffraction image based on an output signal of the semiconductor X-ray detecting means such as the CCD sensor. The two-dimensional diffraction image is a diffraction image that is displayed two-dimensionally or in a plane. The display means may be a video display apparatus such as a CRT (Cathode Ray Tube) or an LCD (Liquid Crystal Display), or a printing display apparatus such as a printer.

DETAILED DESCRIPTION OF THE PREFERRED EMBODIMENTS (First Embodiment)

An embodiment of the present invention will be described, with reference to the accompanying drawings. The present invention is employed in a single-crystal structure analysis apparatus that is one example of the X-ray analysis apparatuses. Needless to say, this invention is not limited to this embodiment.

Figure 1:
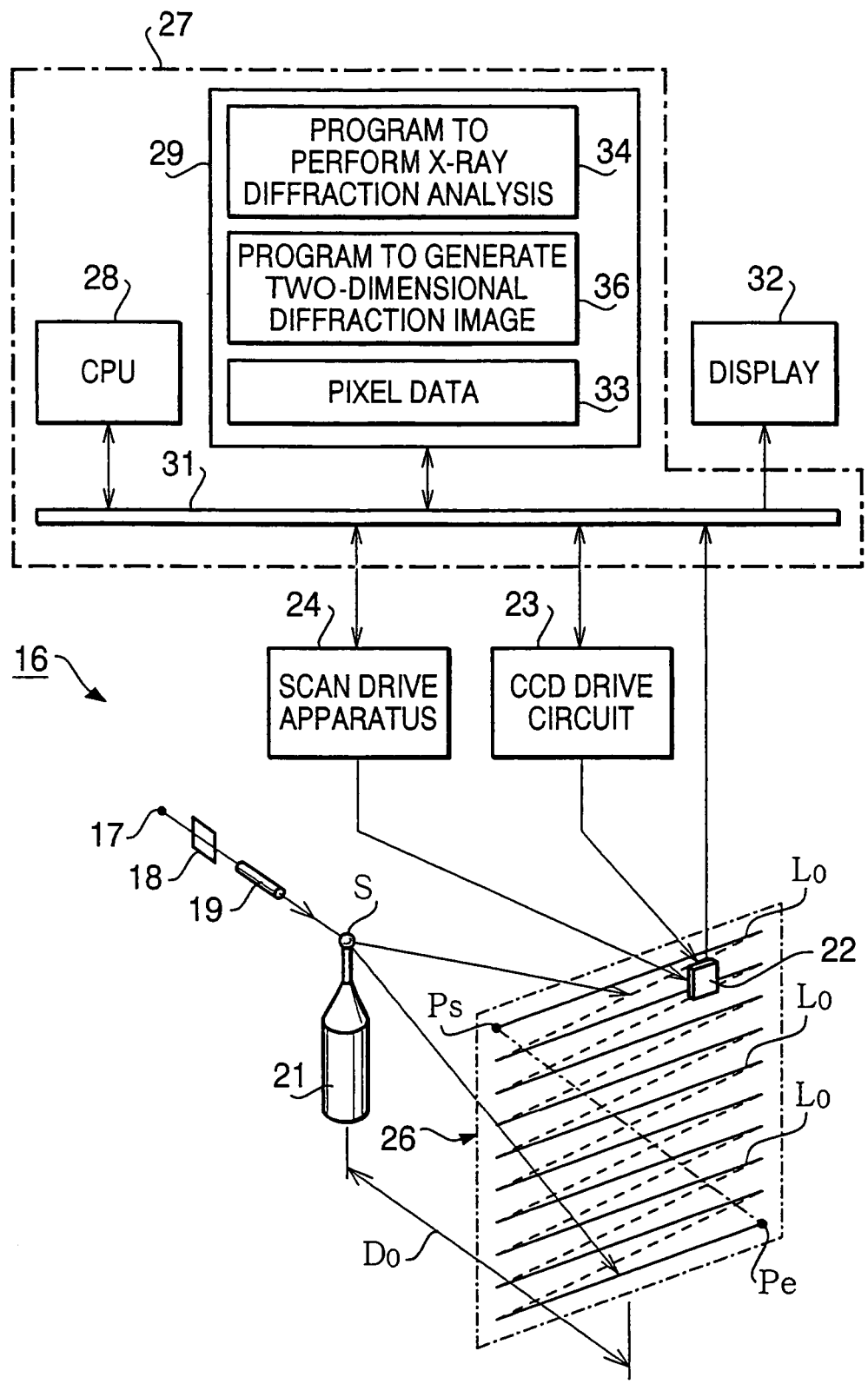
FIG. 1 is a diagram showing an X-ray analysis apparatus according to an embodiment of this invention.
Figure 2:
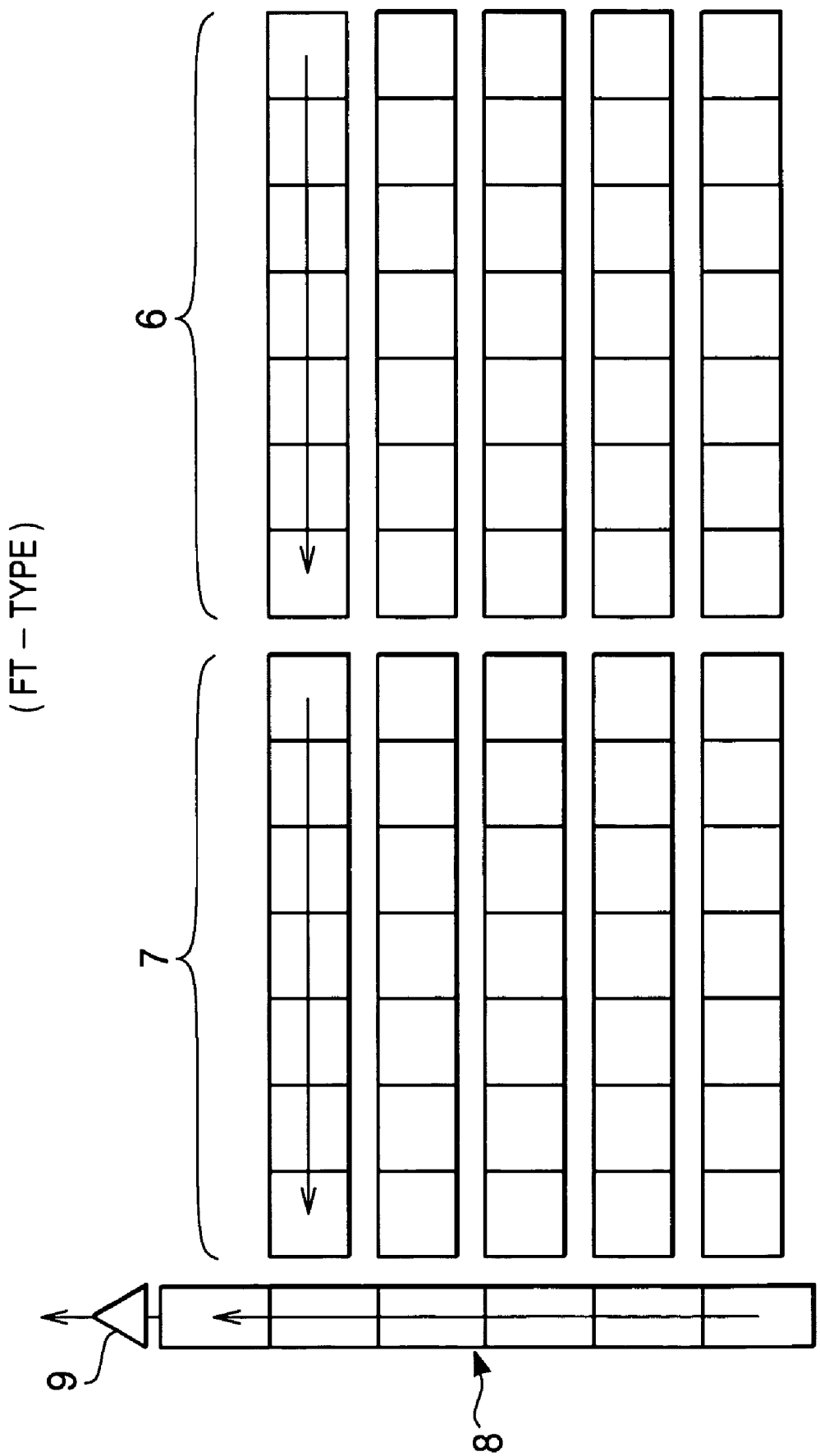
FIG. 2 is a schematic representation of a type of a two-dimensional CCD sensor that can be incorporated in the apparatus of FIG. 1.

FIG. 1 shows a single-crystal structure analysis apparatus 16 that has an X-ray source 17 for generating an X-ray, a monochromator 18 for monochromating an X-ray, a collimator 19 for collimating a diffused X-ray into a parallel X-ray, a goniometer head 21 for supporting a sample 'S', and a two-dimensional CCD sensor 22 that works as a semiconductor X-ray detecting means. The two-dimensional CCD sensor 22 has its pixel size set to be approximately 24 μm×24 μm, and is of the type that can directly detect an X-ray.

Figure 10:
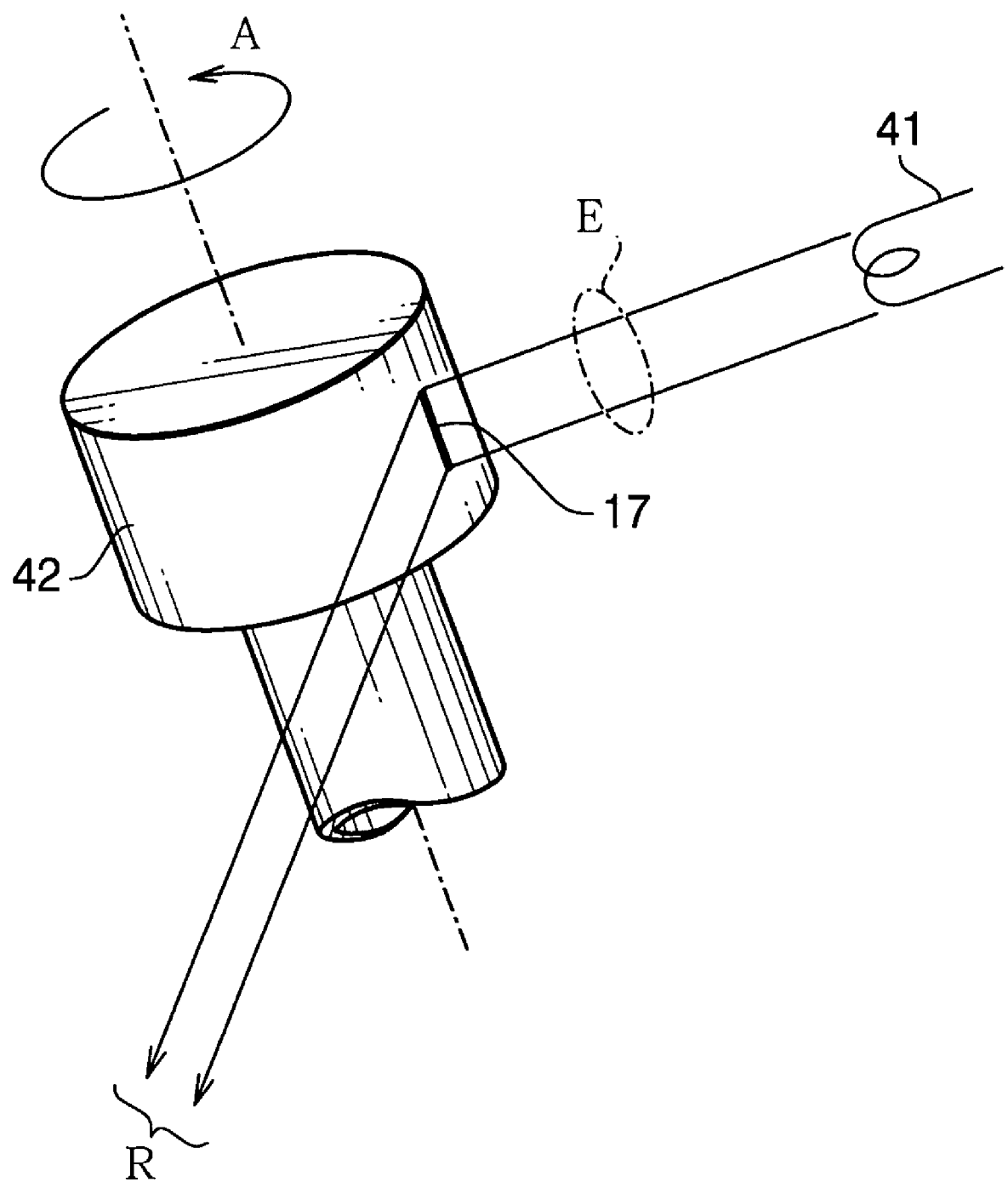
FIG. 10 is a diagram showing an example of an X-ray source.

As shown in FIG. 10, the X-ray source 17 has a filament 41 that is heated by a current running therethrough and emits a thermoelectron 'E', and a target 42 that is so arranged as to face the filament 41 and emits an X-ray 'R' when being hit by the thermoelectron 'E'. Thus emitted X-ray 'R' has its wavelength determined depending on the material of the target 42. The target 42 rotates along an arrow 'A' to be cooled down, if necessary.

The monochromator 18 shown in FIG. 1 is made of single crystal material such as graphite. The collimator 19 may be a pinhole collimator provided with a single pinhole or double pinholes.

Figure 11:
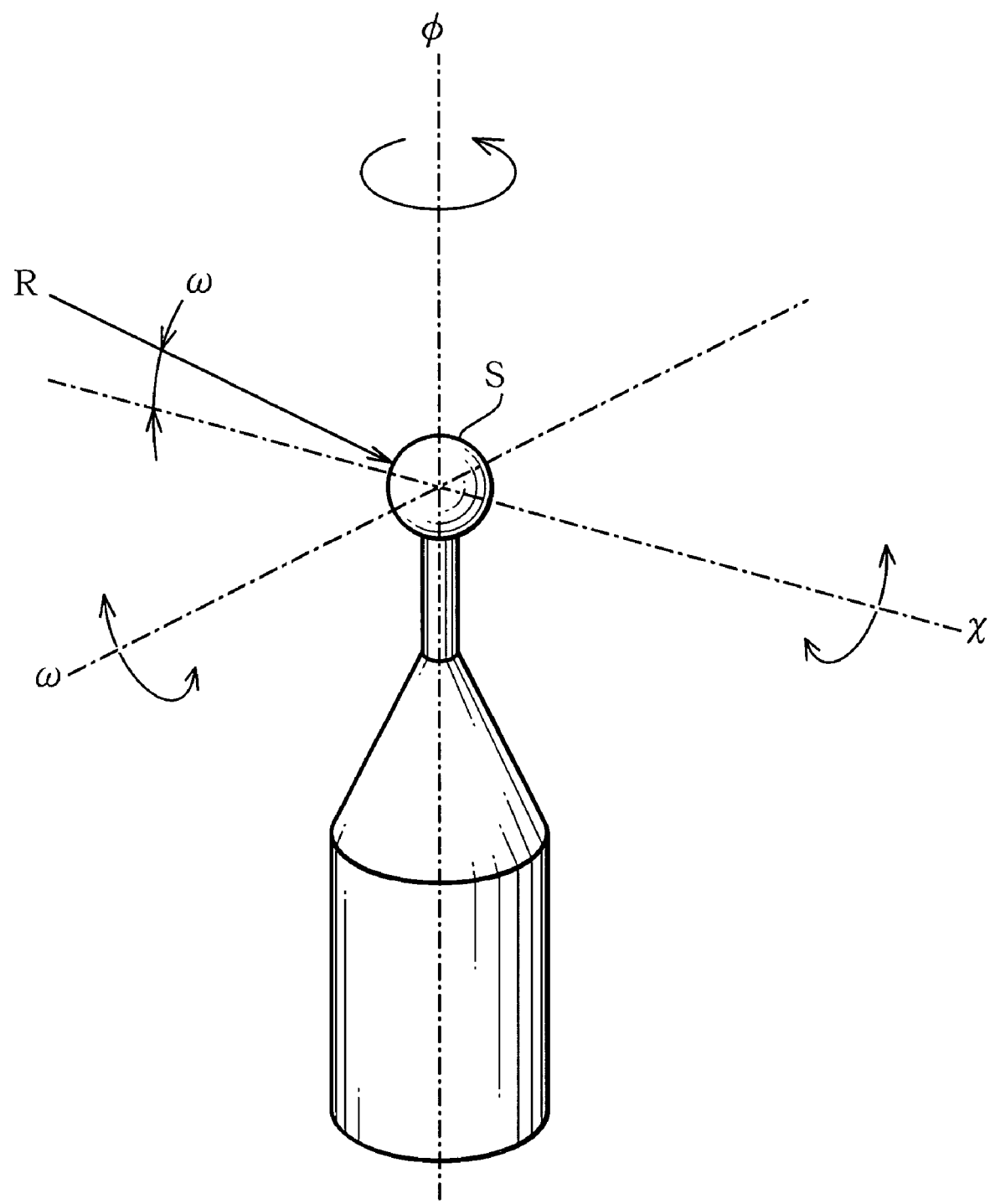
FIG. 11 is a diagram for explaining the function of a goniometer head.

The goniometer head 21 may be a triaxial goniometer head. Using the triaxial goniometer head, as shown in FIG. 11, when some or all of three axis lines or the ω axis line, φ axis line, χ axis line are selected and the sample 'S' is rotated around thus selected axis lines by desired degrees, an arbitrary diffracting plane of the single crystal sample 'S' is directed to an X-ray emitted from the X-ray source 17. Thus the X-ray can be applied to the arbitrary diffracting plane.

The ω axis line is an axis line perpendicular to the center axis line of an X-ray coming to the sample 'S'. The incident angle of the X-ray 'R' with respect to the sample 'S' can be varied by rotating the sample 'S' around the ω axis line. The φ axis line is an axis line perpendicular to the ω axis line which passes through the sample 'S'. The sample 'S' can be rotated in a plane by rotating the sample 'S' around the φ axis line. The χ axis line is an axis line perpendicular to the ω axis line as well as to the φ axis line.

Figure 3:
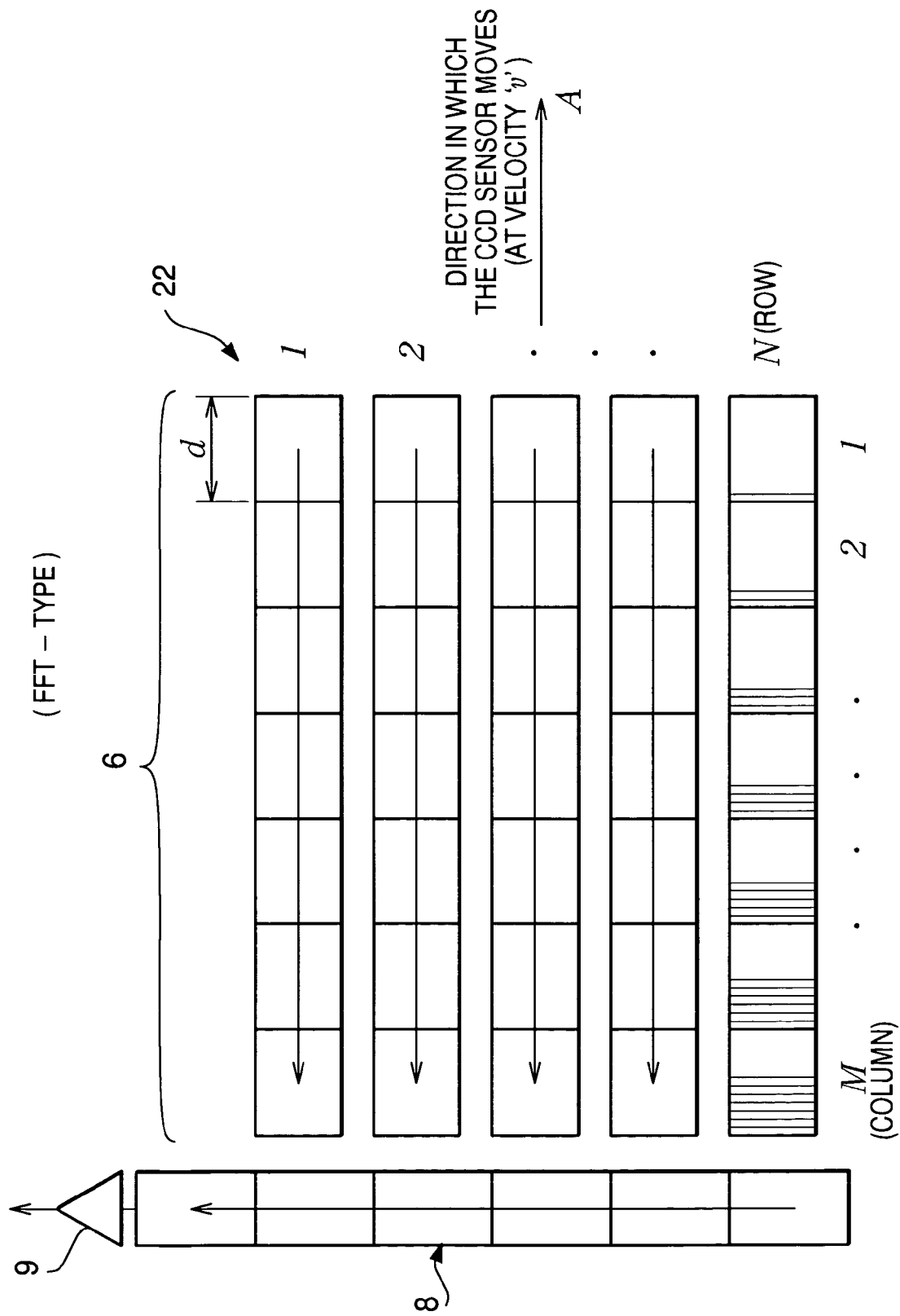
FIG. 3 is a schematic representation of another type of a two-dimensional CCD sensor that can be incorporated in the apparatus of FIG. 1.
Figure 4:
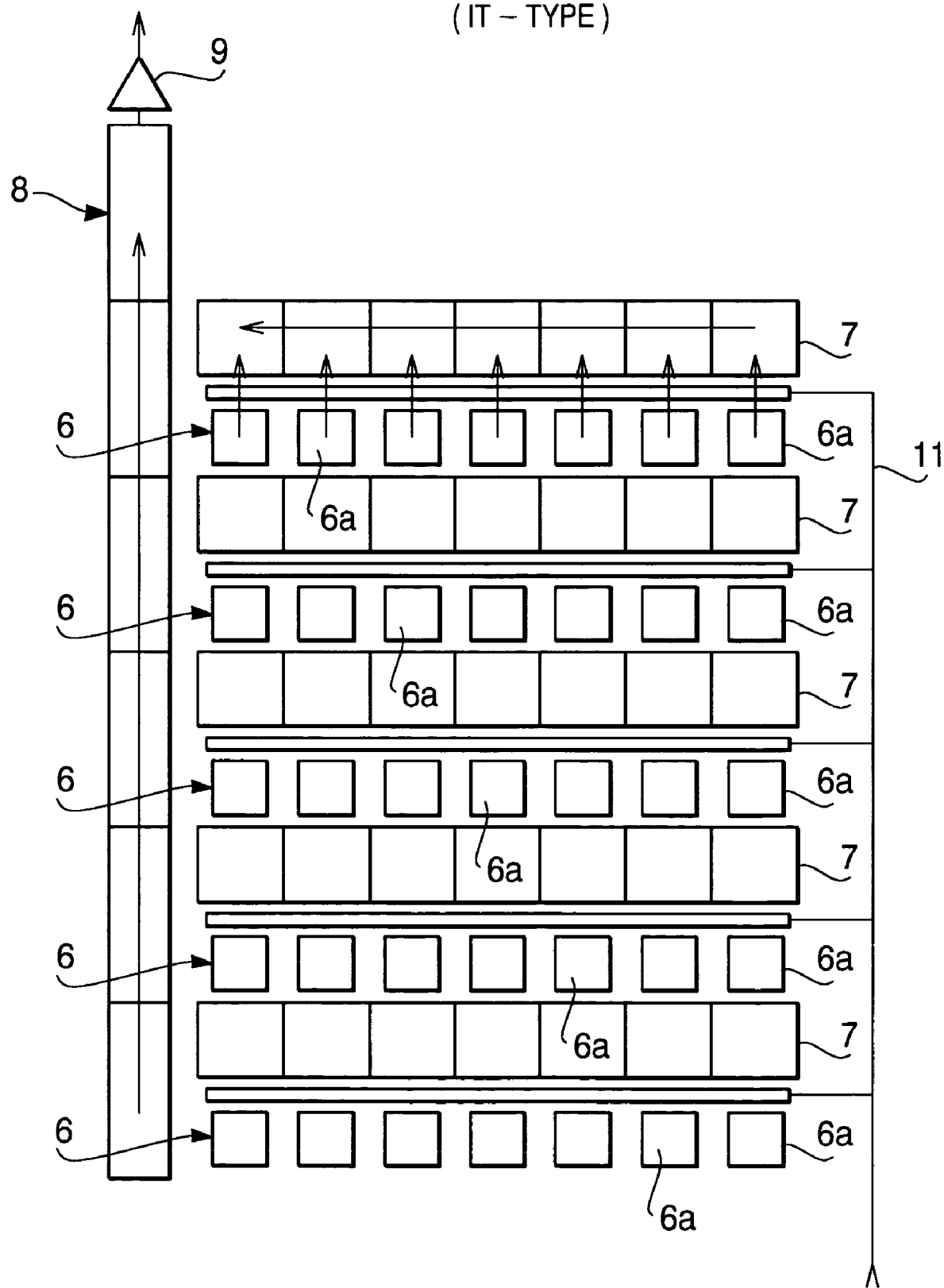
FIG. 4 is a schematic representation of still another type of a two-dimensional CCD sensor that can be incorporated in the apparatus of FIG. 1.
Figure 5:
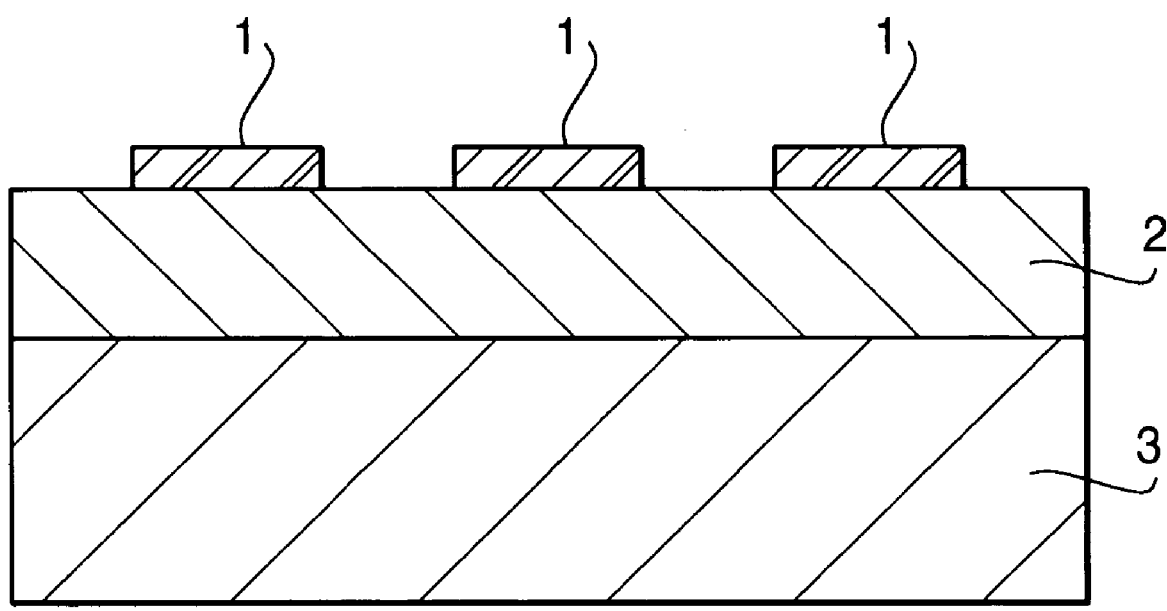
FIG. 5 is a cross sectional view of a two-dimensional CCD sensor, depicting some of the pixels of the two-dimensional CCD sensor.

In this embodiment, the two-dimensional CCD sensor 22 shown in FIG. 1 is an FFT-type CCD sensor that is illustrated in FIG. 3. The two-dimensional CCD sensor 22 is driven by a CCD drive circuit 23 for data processing as is illustrated in FIG. 1. The CCD drive circuit 23 drives the two-dimensional CCD sensor 22 to make it perform so-called TDI (Time Delay Integration) operation. Furthermore, the two-dimensional CCD sensor 22 is driven by a scan drive apparatus 24 to be scan-moved in a scanning plane 26, that is, so moved as to scan in the scanning plane 26.

The scanning plane 26 is a plane that is arranged in space behind the sample 'S' by a predetermined distance $D_0$ when viewed from the X-ray source 17. It is desired that the scanning plane 26 be perpendicular to the optical axis or the center axis of an X-ray coming to the sample 'S'. The scan drive apparatus 24 controls the two-dimensional CCD sensor 22 to make it move along a plurality of scanning lines $L_0$ in the scanning plane 26.

Figure 12:
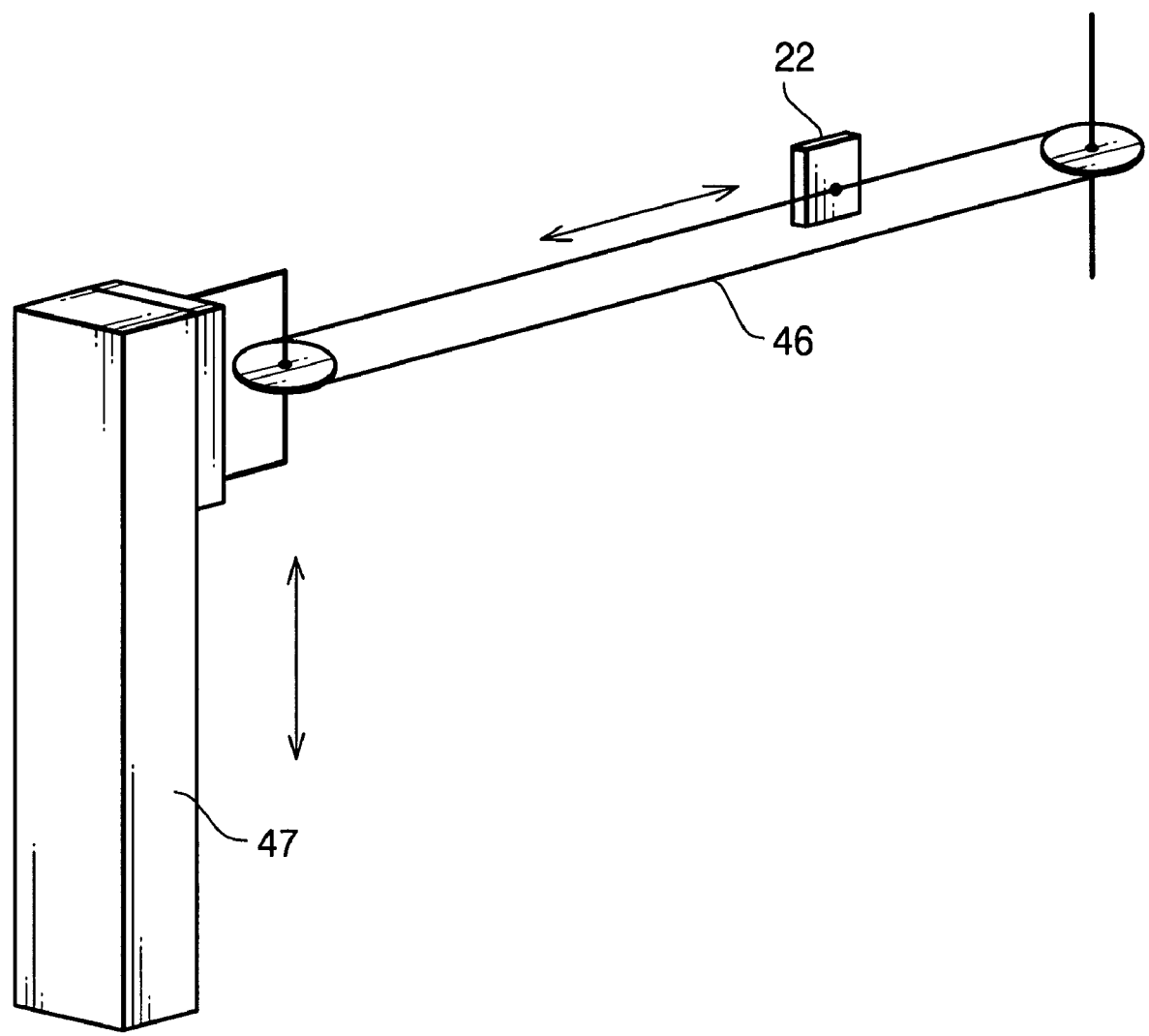
FIG. 12 is a diagram showing an example of an apparatus for scan-moving a CCD sensor.

The scan drive apparatus 24, whose configuration is arbitrarily selected, may have a wire 46 that moves roundly along the horizontal direction, and a drive apparatus 47 that parallelly moves the wire 46 along the vertical direction, as shown in FIG. 12. The X-ray direct detection type CCD is excellent in efficiency of detecting an X-ray, which enables high speed scanning. For example, an image of high S/B ratio (signal-to-background ratio) can be obtained by scanning of 200 seconds over 100 mm×100 mm range.

As shown in FIG. 1, the single-crystal structure analysis apparatus 16 has a controller 27. The controller 27 incorporates a CPU (Central Processing Unit) 28, a storage medium or memory 29, and a bus 31 for transferring various signals. The memory 29 is a semiconductor memory such as a ROM (Read-Only Memory) or a RAM (Random-Access Memory), a mechanical memory such as a hard disk, a CD (Compact Disc) or an MO (Magnetic Optical) disk, or a memory of any other type. The single-crystal structure analysis apparatus 16 further has a display 32. The display 32 is a video display means such as a CRT or an LCD, or a printing means such as a printer.

The memory 29 includes three files 33, 34 and 36. The file 33 stores pixel data output from the CCD sensor 22. The file 34 stores a program that is used to perform X-ray diffraction analysis. The file 36 stores a program that is used to generate a two-dimensional diffraction image from the pixel data stored in the pixel-data file 33. The two-dimensional diffraction image is an image that depicts the result of the X-ray analysis concerning a single crystal two-dimensionally, that is, as a planar image or printed image, and the configuration of the single crystal sample 'S' can be determined by monitoring the two-dimensional diffraction image.

The X-ray diffraction analysis program stored in the file 34 controls the scan drive apparatus 24. More precisely, the X-ray diffraction analysis program makes the two-dimensional CCD sensor 22 move back and forth linearly along the scanning lines $L_0$ over the range of the scanning plane 26 or from the scanning start position $P_s$ to the scanning end position $P_e$. Then, the final desired X-ray image can be obtained by bringing together and displaying thus scanned data. Furthermore, the X-ray diffraction analysis program gives instructions to the CCD drive circuit 23 to make the CCD sensor 22 perform the TDI (Time Delay Integration) operation. In making the CCD sensor 22 perform the TDI operation, the X-ray diffraction analysis program serves to transfer electric charges in the CCD sensor 22 in synchronization with scan-motion velocity of the CCD sensor 22 by the scan drive apparatus 24.

Now, the TDI operation will be explained. The TDI operation is performed on the assumption that the FFT-type CCD sensor of FIG. 3 is employed. It is assumed that the motion velocity of a subject on the receiving surface of the CCD sensor is set to be 'v'. On the other hand, the charge-transfer frequency along the motion direction of the subject or the lateral direction in FIG. 3 is set to be 'f'. Each of the pixels of the CCD sensor 22 has a width 'd'. The transfer of electric charges in the CCD sensor is synchronized with the motion velocity 'v' of the CCD sensor with respect to the subject, thus establishing the following equation:

$$v = f \times d$$

This is the TDI operation. In this way, in the TDI operation, every time electric charges are transferred among plural pixels, data of the same part of the subject is accumulated in the pixels. Thus, when detecting weak electric charges, or when shooting a moving subject, or when the CCD sensor itself moves to shoot a motionless subject, a significantly correct image data can be obtained.

As can be seen from FIG. 3, the input at the first column (the rightmost column) of M columns (columns are arranged along the up and down direction) moves to the second column upon lapse of time 1/f as the CCD sensor 22 moves at velocity 'v' in the direction of an arrow 'A'. Simultaneously, electric charges at the first column are transferred to the second column. The electric charges are thus accumulated in the second column by virtue of photoelectric conversion of data of the same part of a subject. The sequence of these operations is repeated until the electric charges reach the last column (i.e., the M-th column). As a result, signal charges M times as much as is possible with the ordinary charge-transfer not using the TDI operation can be accumulated during this period. The signal charges, thus accumulated, are continuously output, in units of columns, from the horizontal shift register 8 that is provided in the CCD sensor. Thus output signal charges represent data of a two-dimensional image.

In the X-ray analysis apparatus according to this embodiment configured as described above, as shown in FIG. 1, when the X-ray diffraction analysis is started, an X-ray generated from the X-ray source 17 is monochromated by the monochromator 18, collimated by the collimator 19 to be parallel, and is applied to the sample 'S'. At this time, when the Bragg's condition of diffraction is satisfied, a diffracted X-ray emerges from the sample 'S'. The diffracted X-ray travels in the direction along a specific diffraction angle. One of the pixels provided in the light-receiving unit 6 (shown in FIG. 3) of the two-dimensional CCD sensor 22, which is scan-moved in the scanning plane 26 along the scanning lines $L_0$, receives the diffracted X-ray. Upon receipt of the X-ray, this pixel generates an electric charge, which is further accumulated.

The CCD sensor 22 performs the TDI operation and, under the TDI operation, transfers the electric charges in synchronization with its scan-motion velocity. Hence, the signal charges relating to the same diffraction angle are accumulated in one pixel and then in the next pixel. The CCD sensor 22 can always store the correct data about the diffracted X-ray in the pixel even if it is moved at a high speed. The signal charges thus stored in each pixel are transferred from the light-receiving unit 6 to the horizontal shift register 8, in unit of columns. The charges are then stored into the pixel-data file 33 (FIG. 1) through the output unit 9. This acquisition of data terminates after the CCD sensor 22 shown in FIG. 1 is scan-moved from the starting point $P_S$ to the ending point $P_e$. Thus, the data representing the intensities of X-rays diffracted at respective diffraction angles in the scan plane 26 is stored into the pixel-data file 33.

Figure 8:
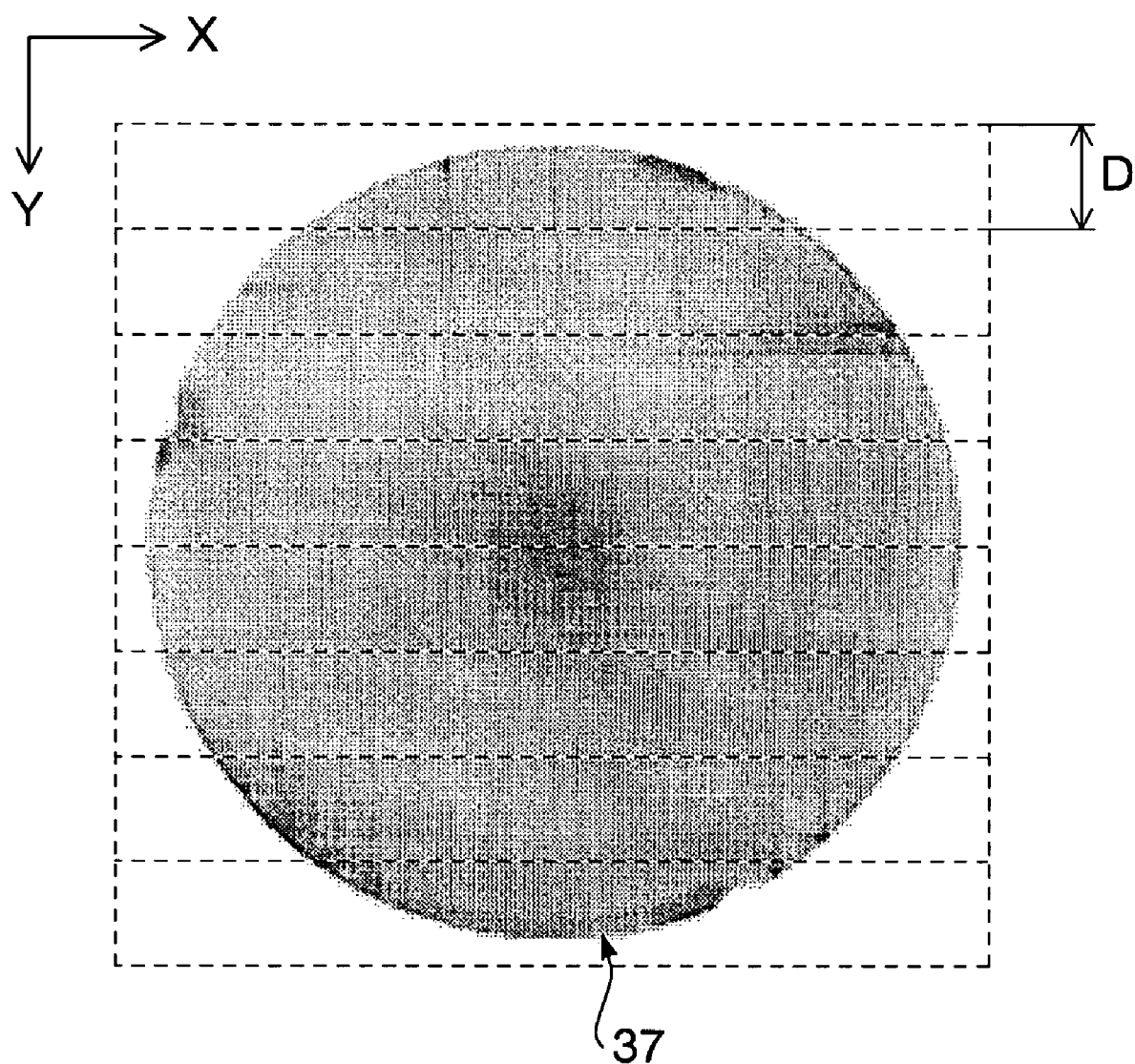
FIG. 8 is a two-dimensional diffraction image obtained by using the X-ray analysis apparatus according to this invention.
Figure 9:
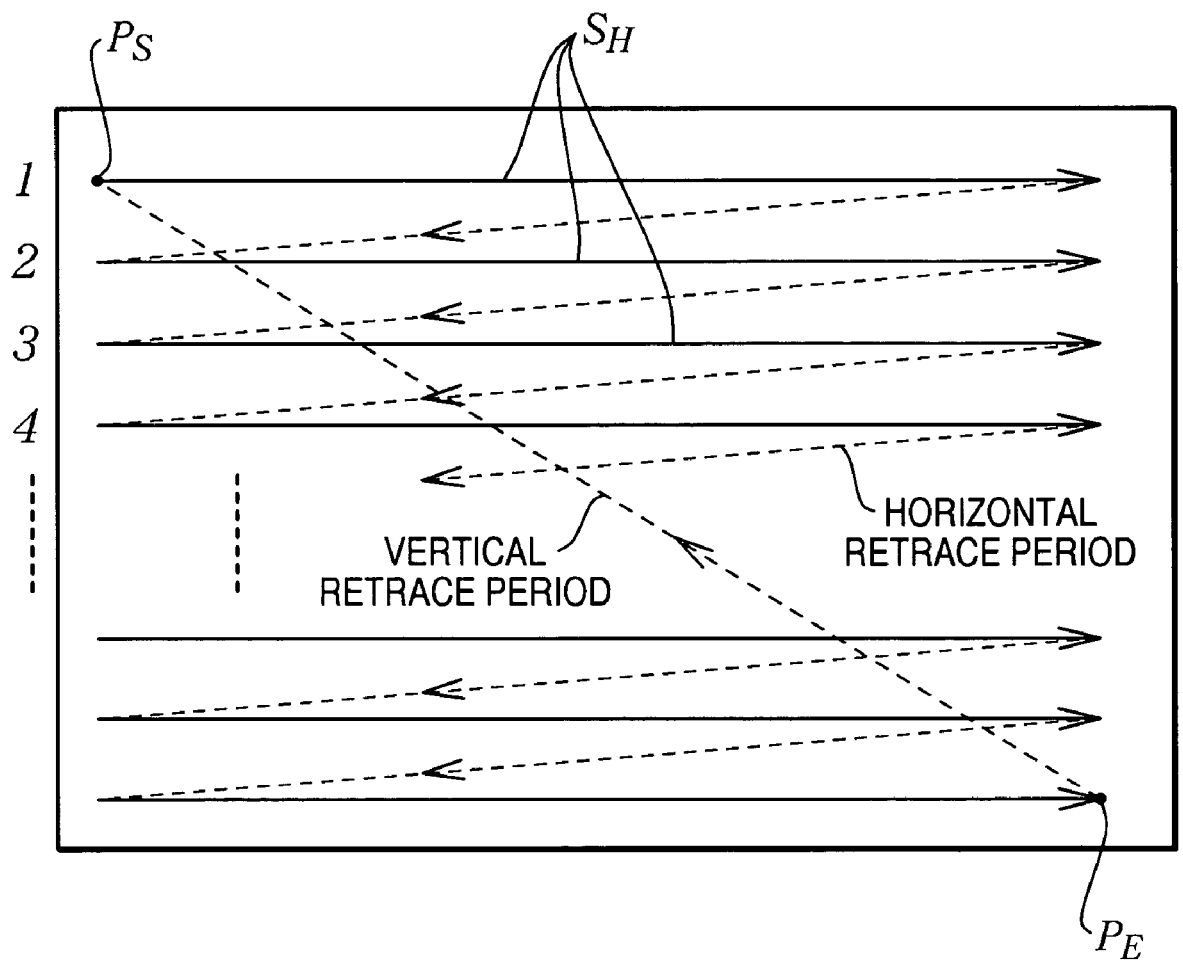
FIG. 9 is a diagram for explaining the function of a CCD sensor.

The CPU 28 executes the program to generate a two-dimensional diffraction image, which is stored in the file 36, to arithmetically operate data that represents a two-dimensional diffraction image from the pixel data stored in the file 33. Thus arithmetically produced two-dimensional diffraction image is displayed on the screen of the display 32 shown in FIG. 1 as an image or character, whenever necessary, as shown in FIG. 8. An observer can monitor thus produced two-dimensional diffraction image to determine the configuration of the single crystal sample 'S'.

(Second Embodiment)

Figure 7:
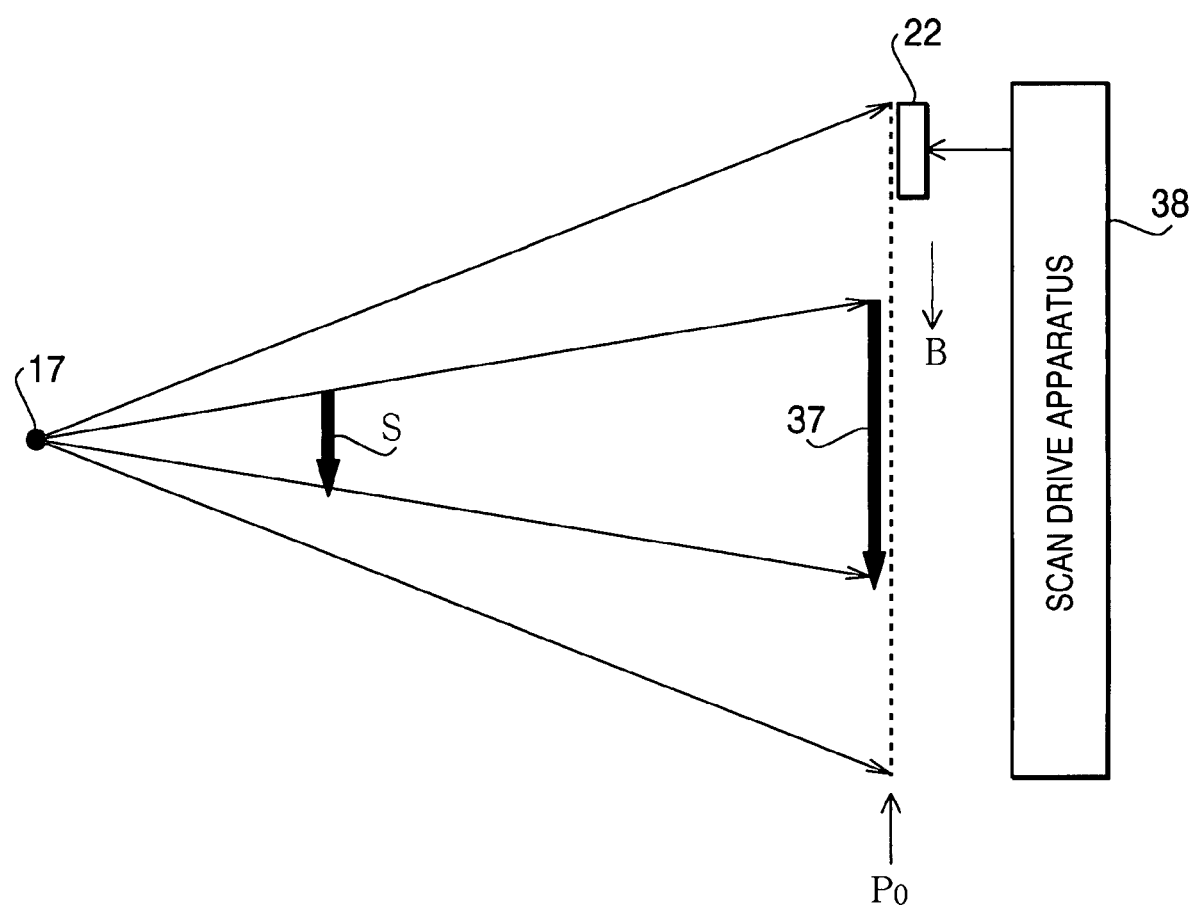
FIG. 7 is a diagram showing an X-ray analysis apparatus according to another embodiment of this invention.

FIG. 7 shows an X-ray analysis apparatus according to another embodiment of the present invention. In this embodiment, the present invention is applied to a projection type X-ray microscope. As shown in FIG. 7, an X-ray emitted from an X-ray source 17 is applied to a sample 'S', and a projected image 37 of the sample 'S' is formed on a projection position $P_0$. The projection position $P_0$ is provided with an X-ray direct detection type CCD sensor 22.

The CCD sensor 22 is driven by a scan drive apparatus 38, and is primarily scan-moved along a direction perpendicular to the sheet surface and is then secondarily scan-moved along a direction of an arrow 'B' over such as 100 mm×100 mm plane range extending along a direction perpendicular to the sheet surface at the projection position $P_0$. Being scan-moved in a5 plane, the CCD sensor 22 can detect the projected image 37. When data obtained by the CCD sensor 22 is displayed two-dimensionally, a two-dimensional diffraction image, for example, as shown in FIG. 8, is obtained.

In the two-dimensional diffraction image, data in an elongated rectangular range D, which is surrounded by a dotted line, is data obtained by one-way scan (or primary scan) along the X direction of the CCD sensor 22. Then, after moving the CCD sensor 22 along the Y direction (or secondary scan direction) by the vertical width of the CCD sensor 22, the primary scan along the X direction is performed again. When data obtained by the first primary scan and data obtained by the second primary scan are brought together, data corresponding to two elongated rectangular ranges can be obtained. Repeating the operation and bringing together thus obtained data, finally, the two-dimensional projected image 37 is obtained, in which a planar X-ray diffraction image is depicted.

Generally, in an X-ray microscope, a sample is placed between a minute X-ray source and a two-dimensional detector to obtain an enlarge image. When improving resolution using this type of X-ray microscope, there are suggested three methods of (1) reducing the size of the X-ray source, (2) raising spatial resolution of the detector, (3) separating the detector from the sample. On the other hand, there is a limit in reducing the size of an X-ray source. When the X-ray source is too small, total output becomes small, which requires long exposure time. When the detector is separated from the sample, scattering of X-rays by air and absorption of X-rays by air are increased, which also requires long analysis time.

As a detector used in an X-ray microscope, there are suggested an X-ray film, a two-dimensional X-ray detector using storage phosphor, and a two-dimensional CCD. As the two-dimensional X-ray detector using storage phosphor, there is known an imaging plate (brand name). The two-dimensional X-ray detector using storage phosphor, which requires long reading time after exposure, is not better suited for high speed analysis. Furthermore, the imaging plate has its resolution set to be approximately 100 μm, which is lower than that of the X-ray direct detection type CCD sensor 22.

Figure 6:
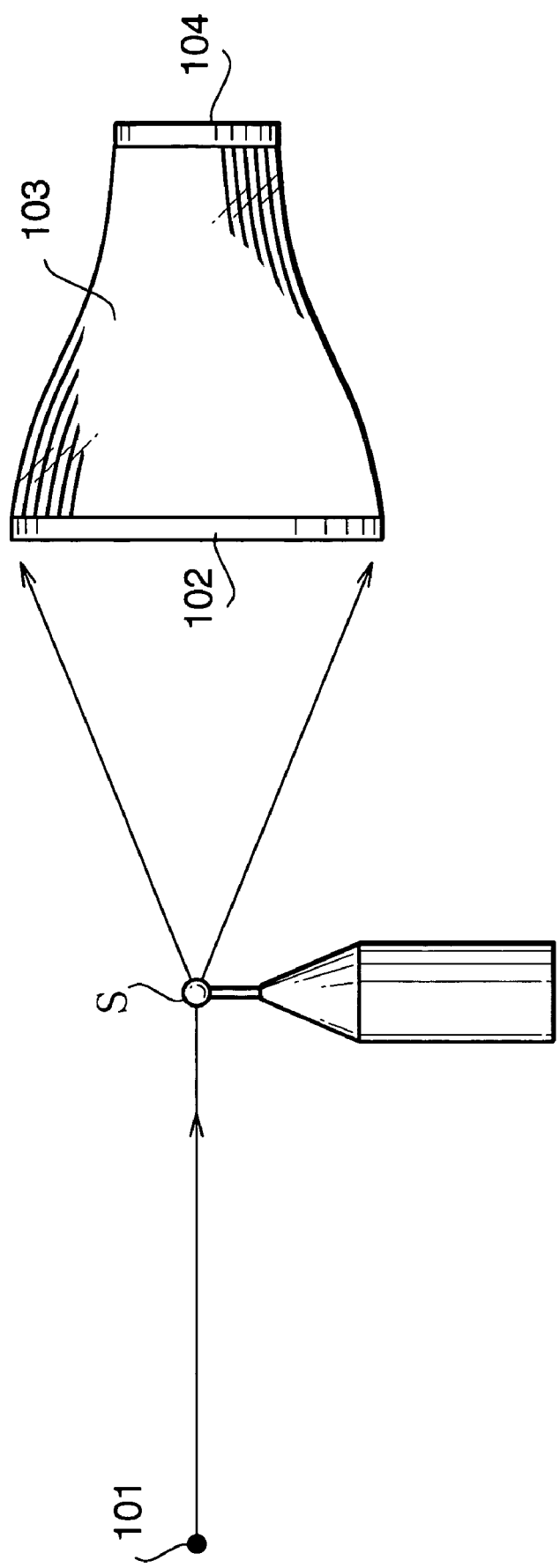
FIG. 6 is a side view of a conventional X-ray analysis apparatus using a two-dimensional CCD sensor.

There is a detector as shown in FIG. 6 that combines the tapered optical fibers and a cooling type CCD sensor, in which a digital image can be obtained on the basis of pixels of the CCD sensor. Such a detector has its spatial resolution set to be approximately 100 μm similar to the resolution of the imaging plate. When obtaining an image of high resolution using the tapered CCD sensor or the imaging plate, it is necessary to separate the detector from the sample. In this case, an X-ray diffracted by the sample has to travel over a long distance before reaching the detector. So, there is a fear that the diffracted X-ray is attenuated during the travel, deteriorating the accuracy.

Furthermore, in case of analysis using the phosphor plate, as shown in the detector of FIG. 6, there is a fear that blur is raised in an image formed on the phosphor plate, gradating the image. In this case, when the image is read out by the CCD sensor, the accuracy of thus read out image may be deteriorated.

Since the X-ray direct detection type CCD sensor 22 employed in the present embodiment has its respective pixel size of plural pixels arranged on the receiving surface thereof set to be significantly small or approximately 24 μm×24 μm, when obtaining an image of the same spatial resolution, it becomes possible to reduce the distance to the sample by half or more as compared with the general CCD sensor. In the analysis using the X-ray direct detection type CCD sensor 22, it is not necessary to convert an X-ray to light using a phosphor plate. So, the X-ray direct detection type CCD sensor 22 is excellent in efficiency of detecting an X-ray. That is, even a low power X-ray can be surely read out.

Furthermore, the X-ray direct detection type CCD sensor 22 that reads an X-ray under the TDI mode has to undergo the raster scanning using an appropriate Y-Z stage since the area to detect an X-ray is small. In this case, being excellent in X-ray detection efficiency, the X-ray direct detection type CCD sensor 22 can undergo high speed scanning. In scanning over 100 mm×100 mm range, an image of high S/B ratio can be obtained by scanning of approximately 200 seconds. Thus, high speed analysis is possible. When the power of an X-ray is high, the analysis time can be further reduced.

(Other Embodiments)

Preferred embodiments of the invention have been described. This invention is not limited to the embodiments, nevertheless. Various modifications can be made within the scope of the invention, which will be defined by the claims set forth later.

For example, the two-dimensional CCD sensor 22 that is an FFT-type one used in the embodiment shown in FIG. 1 may be replaced, if necessary, by a CCD sensor of any other configuration. Although the present invention is employed in the single-crystal structure analysis apparatus in the embodiment shown in FIG. 1, this invention can be applied to an X-ray diffraction apparatus of any other type. Specifically, in the conventional analysis using a two-dimensional X-ray detector such as an X-ray film or storage phosphor film, for example in the topography analysis, the storage phosphor film etc. may be replaced with the semiconductor X-ray detecting means of the present invention. Moreover, the present invention can be applied to any X-ray analysis apparatus other than X-ray diffraction apparatuses.

What is claimed is:

1. An X-ray analysis apparatus in which X-rays emitted from an X-ray source are applied to a sample and semiconductor X-ray detecting means detects the X-rays diffracted by the sample, said X-ray analysis apparatus comprising:

scan-moving means for scan-moving the semiconductor X-ray detecting means in a plane that is arranged behind the sample by a predetermined distance and on which X-rays, diffracted and diverging from the sample, form an X-ray diffraction image the semiconductor X-ray detecting means having an X-ray receiving surface defined by a plurality of pixels arranged in rows and columns, the X-ray receiving surface being smaller than the plane; and charge-transfer signal generating means for generating a charge-transfer signal in the semiconductor X-ray detecting means, every time the semiconductor X-ray detecting means is moved a distance corresponding to a width of one pixel;

wherein motion of the semiconductor X-ray detecting means and the generation of the charge-transfer signal are synchronized with each other to achieve a time delay integration; and the scan-moving means causes the semiconductor X-ray detecting means to move back and forth linearly along a plurality of scanning lines which extend respectively along a horizontal direction and are arranged in parallel to each other along a vertical direction within the plane.

2. The X-ray analysis apparatus according to claim 1, wherein the semiconductor X-ray detecting means has a CCD (Charge Coupled Device) that is a device for transferring, in a semiconductor, signal charges accumulated in a plurality of potential wells, which are arranged in rows and columns on an X-ray receiving surface and which constitute pixels.

3. The X-ray analysis apparatus according to claim 2, wherein the semiconductor X-ray detecting means has:
   a parallel shift register which is composed of the pixels arranged in rows and columns on the X-ray receiving surface; and
   a serial shift register in which the signal charges are transferred in units of pixel columns provided in the parallel shift register.

4. The X-ray analysis apparatus according to claim 3, further comprising display means for displaying a two-dimensional diffraction image from signals output from the semiconductor X-ray detecting means.

5. The X-ray analysis apparatus according to claim 4, wherein the semiconductor X-ray detecting means has an X-ray direct detection type CCD that directly detects an X-ray.

6. The X-ray analysis apparatus according to claim 3, wherein the semiconductor X-ray detecting means has an X-ray direct detection type CCD that directly detects an X-ray.

7. The X-ray analysis apparatus according to claim 2, further comprising display means for displaying a two-dimensional diffraction image from signals output from the semiconductor X-ray detecting means.

8. The X-ray analysis apparatus according to claim 2, wherein the semiconductor X-ray detecting means has an X-ray direct detection type CCD that directly detects an X-ray.

9. The X-ray analysis apparatus according to claim 1, wherein the semiconductor X-ray detecting means has:
   a parallel shift register which is composed of the pixels arranged in rows and columns on the X-ray receiving surface; and
   a serial shift register in which the signal charges are transferred in units of pixel columns provided in the parallel shift register.

10. The X-ray analysis apparatus according to claim 1, further comprising display means for displaying a two-dimensional diffraction image from signals output from the semiconductor X-ray detecting means.

11. The X-ray analysis apparatus according to claim 1, wherein the semiconductor X-ray detecting means has an X-ray direct detection type CCD that directly detects an X-ray.

* * * * *